United States Patent
Daly et al.

(10) Patent No.: US 9,901,470 B2
(45) Date of Patent: Feb. 27, 2018

(54) METHODS OF REPOSITIONING A TRANSCATHETER HEART VALVE AFTER FULL DEPLOYMENT

(71) Applicant: St. Jude Medical, Cardiology Division, Inc., St. Paul, MN (US)

(72) Inventors: Jacob John Daly, Blaine, MN (US); Aaron J. Chalekian, Savage, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 160 days.

(21) Appl. No.: 14/096,405

(22) Filed: Dec. 4, 2013

(65) Prior Publication Data

US 2014/0249564 A1  Sep. 4, 2014

Related U.S. Application Data

(60) Provisional application No. 61/771,493, filed on Mar. 1, 2013.

(51) Int. Cl.
*A61F 2/06* (2013.01)
*A61F 2/958* (2013.01)
(Continued)

(52) U.S. Cl.
CPC ............ *A61F 2/958* (2013.01); *A61B 17/221* (2013.01); *A61B 17/22032* (2013.01);
(Continued)

(58) Field of Classification Search
CPC ........ A61F 2/95; A61F 2/2427; A61F 2/2439; A61F 2002/9511; A61F 2002/9528;
(Continued)

(56) References Cited

U.S. PATENT DOCUMENTS 3,657,744 A   4/1972   Ersek
4,275,469 A   6/1981   Gabbay
(Continued)

FOREIGN PATENT DOCUMENTS

DE   19857887 A1   7/2000
DE   10121210 A1   11/2002
(Continued)

OTHER PUBLICATIONS

Ruis, Carlos, Overview of PRE-CE Mark Transcatheter Aortic Valve Technologies, Euro PCR (powerpoint)—dated May 25, 2010.
(Continued)

*Primary Examiner* — Melanie Tyson
(74) *Attorney, Agent, or Firm* — Lerner, David, Littenberg, Krumholz & Mentlik, LLP

(57) ABSTRACT

A device for repositioning an implant within a lumen of a subject including (a) a catheter having forward and rearward ends and a collapsible and expansible stop element mounted adjacent the forward end of the catheter, the stop element being adapted to engage a wall of the lumen when expanded and to provide one or more passages extending from a rear side of the stop element to a forward side of the stop element when the stop element is expanded and engaged with the wall of the lumen and (b) one or more snares, each snare having engagement features, the stop element and the snares being constructed and arranged so that the snares can be positioned extending through the one or more passages with their engagement features forward of the stop element.

4 Claims, 6 Drawing Sheets

(51) Int. Cl.
*A61B 17/22* (2006.01)
*A61B 17/221* (2006.01)
*A61F 2/24* (2006.01)
*A61F 2/95* (2013.01)
*A61B 17/00* (2006.01)

(52) U.S. Cl.
CPC .............. *A61B 2017/00358* (2013.01); *A61B 2017/22035* (2013.01); *A61B 2017/22069* (2013.01); *A61F 2/2427* (2013.01); *A61F 2002/9534* (2013.01)

(58) Field of Classification Search
CPC ....... A61F 2002/9534; A61B 17/22031; A61B 2017/2212
See application file for complete search history.

(56) References Cited

U.S. PATENT DOCUMENTS

| | | |
|---|---|---|
| 4,491,986 A | 1/1985 | Gabbay |
| 4,759,758 A | 7/1988 | Gabbay |
| 4,878,906 A | 11/1989 | Lindemann et al. |
| 4,922,905 A | 5/1990 | Strecker |
| 4,994,077 A | 2/1991 | Dobben |
| 5,411,552 A | 5/1995 | Andersen et al. |
| 5,480,423 A | 1/1996 | Ravenscroft et al. |
| 5,843,167 A | 12/1998 | Dwyer et al. |
| 5,855,601 A | 1/1999 | Bessler et al. |
| 5,935,163 A | 8/1999 | Gabbay |
| 5,961,549 A | 10/1999 | Nguyen et al. |
| 6,077,297 A | 6/2000 | Robinson et al. |
| 6,083,257 A | 7/2000 | Taylor et al. |
| 6,090,140 A | 7/2000 | Gabbay |
| 6,214,036 B1 | 4/2001 | Letendre et al. |
| 6,264,691 B1 | 7/2001 | Gabbay |
| 6,267,783 B1 | 7/2001 | Letendre et al. |
| 6,368,348 B1 | 4/2002 | Gabbay |
| 6,419,695 B1 | 7/2002 | Gabbay |
| 6,468,660 B2 | 10/2002 | Ogle et al. |
| 6,488,702 B1 | 12/2002 | Besselink |
| 6,517,576 B2 | 2/2003 | Gabbay |
| 6,533,810 B2 | 3/2003 | Hankh et al. |
| 6,582,464 B2 | 6/2003 | Gabbay |
| 6,610,088 B1 | 8/2003 | Gabbay |
| 6,623,518 B2 | 9/2003 | Thompson et al. |
| 6,685,625 B2 | 2/2004 | Gabbay |
| 6,692,484 B1 * | 2/2004 | Karpiel ............ A61B 17/22031 600/31 |
| 6,719,789 B2 | 4/2004 | Cox |
| 6,730,118 B2 | 5/2004 | Spenser et al. |
| 6,783,556 B1 | 8/2004 | Gabbay |
| 6,790,230 B2 | 9/2004 | Beyersdorf et al. |
| 6,814,746 B2 | 11/2004 | Thompson et al. |
| 6,830,584 B1 | 12/2004 | Seguin |
| 6,869,444 B2 | 3/2005 | Gabbay |
| 6,893,460 B2 | 5/2005 | Spenser et al. |
| 6,908,481 B2 | 6/2005 | Cribier |
| 7,018,406 B2 | 3/2006 | Seguin et al. |
| 7,025,780 B2 | 4/2006 | Gabbay |
| 7,137,184 B2 | 11/2006 | Schreck |
| 7,160,322 B2 | 1/2007 | Gabbay |
| 7,247,167 B2 | 7/2007 | Gabbay |
| 7,267,686 B2 | 9/2007 | DiMatteo et al. |
| 7,311,730 B2 | 12/2007 | Gabbay |
| 7,374,573 B2 | 5/2008 | Gabbay |
| 7,381,218 B2 | 6/2008 | Schreck |
| 7,452,371 B2 | 11/2008 | Pavcnik et al. |
| 7,510,572 B2 | 3/2009 | Gabbay |
| 7,524,331 B2 | 4/2009 | Birdsall |
| RE40,816 E | 6/2009 | Taylor et al. |
| 7,585,321 B2 | 9/2009 | Cribier |
| 7,682,390 B2 | 3/2010 | Seguin |
| 7,731,742 B2 | 6/2010 | Schlick et al. |
| 7,803,185 B2 | 9/2010 | Gabbay |
| 7,846,203 B2 | 12/2010 | Cribier |
| 7,846,204 B2 | 12/2010 | Letac et al. |
| 7,914,569 B2 | 3/2011 | Nguyen et al. |
| D648,854 S | 11/2011 | Braido |
| D652,926 S | 1/2012 | Braido |
| D652,927 S | 1/2012 | Braido et al. |
| D653,341 S | 1/2012 | Braido et al. |
| D653,342 S | 1/2012 | Braido et al. |
| D653,343 S | 1/2012 | Ness et al. |
| D654,169 S | 2/2012 | Braido |
| D654,170 S | 2/2012 | Braido et al. |
| D660,432 S | 5/2012 | Braido |
| D660,433 S | 5/2012 | Braido et al. |
| D660,967 S | 5/2012 | Braido et al. |
| 2002/0036220 A1 | 3/2002 | Gabbay |
| 2003/0023303 A1 | 1/2003 | Palmaz et al. |
| 2003/0050694 A1 | 3/2003 | Yang et al. |
| 2003/0130726 A1 | 7/2003 | Thorpe et al. |
| 2004/0049262 A1 | 3/2004 | Obermiller et al. |
| 2004/0093075 A1 | 5/2004 | Kuehne |
| 2004/0210304 A1 | 10/2004 | Seguin et al. |
| 2005/0096726 A1 | 5/2005 | Sequin et al. |
| 2005/0137695 A1 | 6/2005 | Salahieh et al. |
| 2005/0137697 A1 | 6/2005 | Salahieh et al. |
| 2005/0256566 A1 | 11/2005 | Gabbay |
| 2006/0008497 A1 | 1/2006 | Gabbay |
| 2006/0074484 A1 | 4/2006 | Huber |
| 2006/0122692 A1 | 6/2006 | Gilad et al. |
| 2006/0149360 A1 | 7/2006 | Schwammenthal et al. |
| 2006/0173532 A1 | 8/2006 | Flagle et al. |
| 2006/0178740 A1 | 8/2006 | Stacchino et al. |
| 2006/0206202 A1 | 9/2006 | Bonhoeffer et al. |
| 2006/0241744 A1 | 10/2006 | Beith |
| 2006/0241745 A1 | 10/2006 | Solem |
| 2006/0259120 A1 | 11/2006 | Vongphakdy et al. |
| 2006/0259137 A1 | 11/2006 | Artof et al. |
| 2006/0265056 A1 | 11/2006 | Nguyen et al. |
| 2006/0276813 A1 | 12/2006 | Greenberg |
| 2007/0010876 A1 | 1/2007 | Salahieh et al. |
| 2007/0027520 A1 * | 2/2007 | Sherburne ............... A61F 2/958 623/1.11 |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0067029 A1 | 3/2007 | Gabbay |
| 2007/0093890 A1 | 4/2007 | Eliasen et al. |
| 2007/0100435 A1 | 5/2007 | Case et al. |
| 2007/0118210 A1 | 5/2007 | Pinchuk |
| 2007/0213813 A1 | 9/2007 | Von Segesser et al. |
| 2007/0233228 A1 | 10/2007 | Eberhardt et al. |
| 2007/0244545 A1 | 10/2007 | Birdsall et al. |
| 2007/0244552 A1 | 10/2007 | Salahieh et al. |
| 2007/0288087 A1 | 12/2007 | Fearnot et al. |
| 2008/0021552 A1 | 1/2008 | Gabbay |
| 2008/0039934 A1 | 2/2008 | Styrc |
| 2008/0071369 A1 | 3/2008 | Tuval et al. |
| 2008/0082164 A1 | 4/2008 | Friedman |
| 2008/0097595 A1 | 4/2008 | Gabbay |
| 2008/0114452 A1 | 5/2008 | Gabbay |
| 2008/0125853 A1 | 5/2008 | Bailey et al. |
| 2008/0140189 A1 | 6/2008 | Nguyen et al. |
| 2008/0147183 A1 | 6/2008 | Styrc |
| 2008/0154355 A1 | 6/2008 | Benichou et al. |
| 2008/0154356 A1 | 6/2008 | Obermiller et al. |
| 2008/0243245 A1 | 10/2008 | Thambar et al. |
| 2008/0255662 A1 | 10/2008 | Stacchino et al. |
| 2008/0262592 A1 * | 10/2008 | Jordan ..................... A61F 2/95 623/1.11 |
| 2008/0262602 A1 | 10/2008 | Wilk et al. |
| 2008/0269879 A1 | 10/2008 | Sathe et al. |
| 2009/0112309 A1 | 4/2009 | Jaramillo et al. |
| 2009/0138079 A1 | 5/2009 | Tuval et al. |
| 2009/0157161 A1 * | 6/2009 | Desai ...................... A61F 2/95 623/1.11 |
| 2010/0004740 A1 | 1/2010 | Seguin et al. |
| 2010/0036484 A1 | 2/2010 | Hariton et al. |
| 2010/0049306 A1 | 2/2010 | House et al. |
| 2010/0087907 A1 | 4/2010 | Lattouf |
| 2010/0131055 A1 | 5/2010 | Case et al. |

(56) References Cited

U.S. PATENT DOCUMENTS

| | | |
|---|---|---|
| 2010/0168778 A1 | 7/2010 | Braido |
| 2010/0168839 A1 | 7/2010 | Braido et al. |
| 2010/0185277 A1 | 7/2010 | Braido et al. |
| 2010/0191326 A1 | 7/2010 | Alkhatib |
| 2010/0204781 A1 | 8/2010 | Alkhatib |
| 2010/0204785 A1 | 8/2010 | Alkhatib |
| 2010/0217382 A1 | 8/2010 | Chau et al. |
| 2010/0249911 A1 | 9/2010 | Alkhatib |
| 2010/0249923 A1 | 9/2010 | Alkhatib et al. |
| 2010/0286768 A1 | 11/2010 | Alkhatib |
| 2010/0298931 A1 | 11/2010 | Quadri et al. |
| 2011/0029072 A1 | 2/2011 | Gabbay |

FOREIGN PATENT DOCUMENTS

| | | |
|---|---|---|
| DE | 202008009610 U1 | 12/2008 |
| EP | 0850607 A1 | 7/1998 |
| EP | 1000590 A1 | 5/2000 |
| EP | 1360942 A1 | 11/2003 |
| EP | 1584306 A1 | 10/2005 |
| EP | 1598031 A2 | 11/2005 |
| FR | 2847800 A1 | 6/2004 |
| FR | 2850008 A1 | 7/2004 |
| WO | 9117720 A1 | 11/1991 |
| WO | 9716133 A1 | 5/1997 |
| WO | 9832412 A2 | 7/1998 |
| WO | 9913801 A1 | 3/1999 |
| WO | 2001028459 A1 | 4/2001 |
| WO | 0149213 A2 | 7/2001 |
| WO | 2001054625 A1 | 8/2001 |
| WO | 2001056500 A2 | 8/2001 |
| WO | 2001076510 A2 | 10/2001 |
| WO | 0236048 A1 | 5/2002 |
| WO | 0247575 A2 | 6/2002 |
| WO | 03047468 A1 | 6/2003 |
| WO | 06073626 A2 | 7/2006 |
| WO | 07071436 A2 | 6/2007 |
| WO | 2007071436 A2 | 6/2007 |
| WO | 08070797 A2 | 6/2008 |
| WO | 2008070797 A2 | 6/2008 |
| WO | 10008548 A2 | 1/2010 |
| WO | 10008549 A1 | 1/2010 |
| WO | 10096176 A1 | 8/2010 |
| WO | 10098857 A1 | 9/2010 |

OTHER PUBLICATIONS

Quaden, Rene, et al., Percutaneous aortic valve replacement: resection before implantation, 836-840, European J. of Cardio-thoracic Surgery 27, (2005) 836-840.

Knudsen, L.L. et al., Catheter-implanted prosthetic heart valves, The International Journal of Artificial Organs, vol. 16, No. 5, 1993, pp. 253-262.

Moazami, Nader, et al. Transluminal Aortic Valve Placement, ASAIO Journal, 1996; 42:M381-M385.

Andersen, H.R., Transluminal Catheter Implanted Prosthetic Heart Valves, International Journal of Angiology 7:102-106 (1998).

Andersen, H.R. et al., Transluminal implantation of artificial heart valves, European Heart Journal (1992) 13, 704-708.

Zegdi, Rachid, MD, PhD. et al., Is It Reasonable to Treat All Calcified Stenotic Aortic Valves With a Valved Stent?, 579-584, J. of the American College of Cardiology, vol. 51, No. 5, 2008.

U.S. Appl. No. 29/375,243, filed Sep. 20, 2010.

U.S. Appl. No. 29/375,260, filed Sep. 20, 2010.

\* cited by examiner

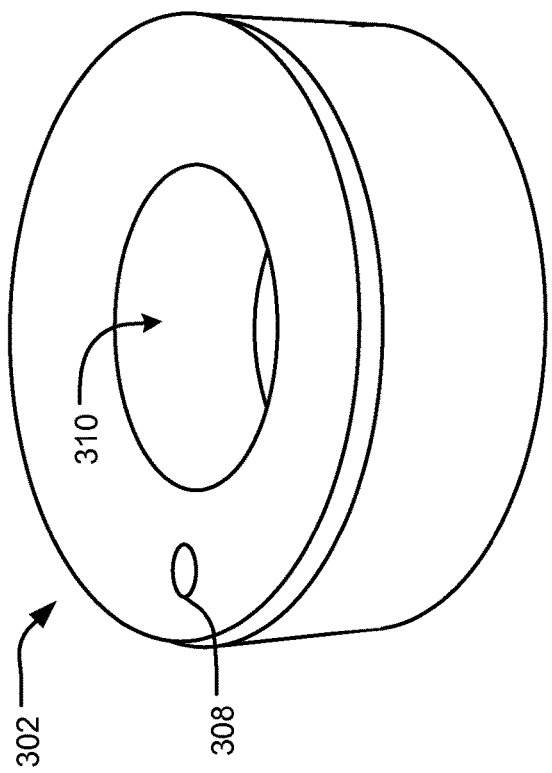
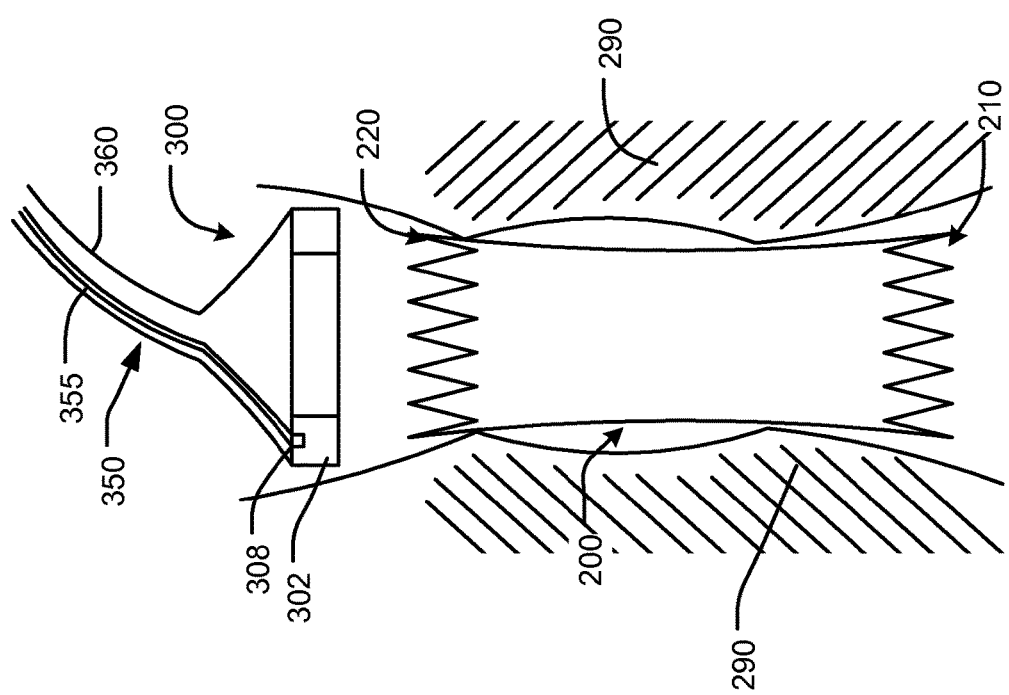
FIG. 3B
FIG. 3A

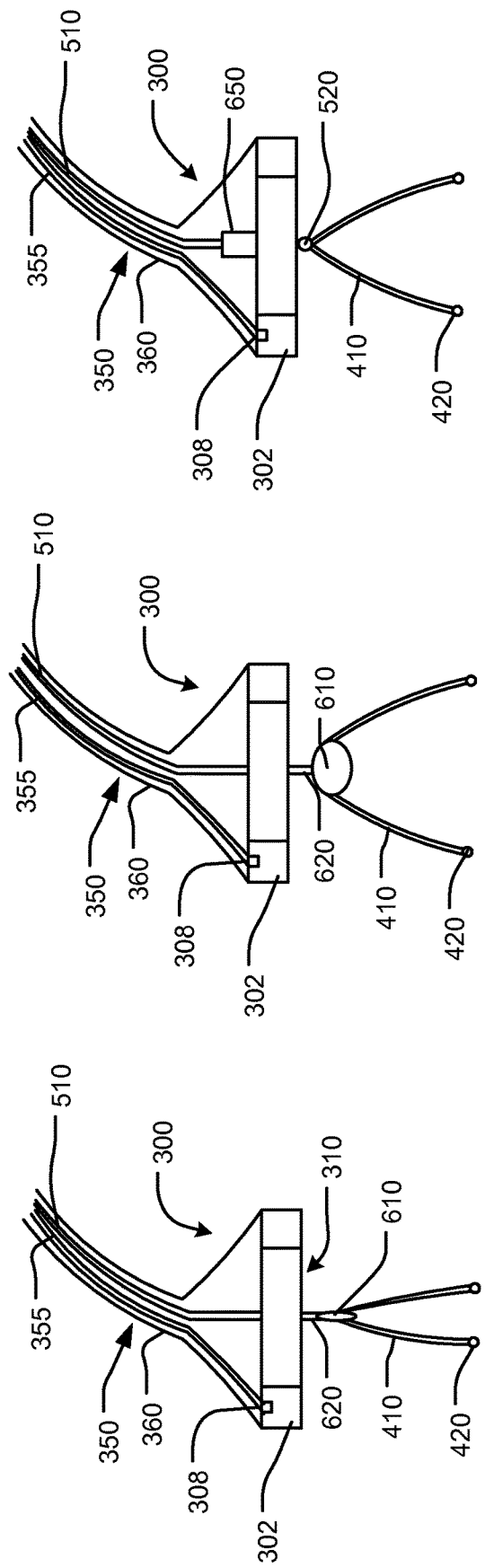

METHODS OF REPOSITIONING A TRANSCATHETER HEART VALVE AFTER FULL DEPLOYMENT

CROSS-REFERENCES TO RELATED APPLICATIONS

The present application claims the benefit of the filing date of U.S. Provisional Patent Application No. 61/771,493 filed Mar. 1, 2013, the disclosure of which is hereby incorporated herein by reference.

BACKGROUND OF THE INVENTION

The present invention relates to heart valve replacement and, in particular, to collapsible prosthetic heart valves. More particularly, the present invention relates to devices and methods for repositioning of collapsible prosthetic heart valves.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent or a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, and then expanding a balloon positioned within the valve stent. For self-expanding valves, on the other hand, the stent automatically expands as the sheath covering the valve is withdrawn.

Despite the various improvements that have been made to the collapsible prosthetic heart valve delivery process, conventional delivery devices, systems, and methods suffer from several shortcomings. For example, in conventional delivery devices for self-expanding valves, clinical success of the valve is dependent on accurate positioning, anchoring and acceptable valve performance. Inaccurate positioning increases risks such as valve migration, which may result in severe complications due to obstruction of the left ventricular outflow tract and may even result in patient death. Inaccurate positioning may further limit proper performance of the valve assembly. Additionally, improper positioning of a prosthetic heart valve may cause extended compression and/or stent deformation that affect valve durability.

In conventional devices, once the prosthetic heart valve has been fully deployed, it is difficult to reposition the valve without resheathing the valve and redeploying. One risk in repositioning a fully deployed valve is pushing the prosthetic heart valve into a dangerous location such as, for example, the ascending aorta due to lack of control.

There, therefore, is a need for further improvements to the devices, systems, and methods for transcatheter delivery and positioning of collapsible prosthetic heart valves. Specifically, there is a need for further improvements to the devices, systems, and methods for accurately positioning a prosthetic heart valve within the vasculature of a patient. Such positioning devices will help to reduce the risks associated with valve migration and improper valve positioning. Among other advantages, the present invention may address one or more of these needs.

SUMMARY OF THE INVENTION

In some embodiments, a method of repositioning an implant engaged in a lumen of a mammalian subject includes (a) inserting an expansible stop element into the lumen and expanding the stop element into engagement with a wall of the lumen at a location offset from the implant, (b) inserting one or more snares into the lumen and engaging the snares with the implant, (c) while the snares are engaged with the implant, moving the snares so as to move the engaged implant toward the stop element and (d) disengaging the snares from the implant and removing the snares and stop element from the lumen.

In some examples, the step of moving the snares is performed so as to move the implant into abutment with the stop element. The implant may include a stent and the step of engaging the snares with the stent includes engaging the snares with the stent. The implant may include a valve mounted to the stent for controlling flow through the lumen. The lumen may be a blood vessel. The lumen may be the aortic root. The stop element may define one or more passages through the stop element, and step (b) may include advancing the snares through the one or more passages. In some examples, when the stop element is in an expanded state and engaged with the wall of the lumen, the stop element may define one or more passages between the stop element and the wall of the lumen, and step (b) may include advancing the snares through the one or more passages.

In some examples, the stop element may include a stop balloon and the step of expanding the stop element into engagement with the wall of the lumen may include inflating the balloon. The method may further include a conduit in fluid communication with the inside of the stop balloon for delivering a fluid to inflate the stop balloon. The one or more snares may include a plurality of snares connected to an elongated probe and step (b) includes advancing the probe in a forward direction through the lumen while the snares are in collapsed condition with engagement features on the snares adjacent one another and then moving the snares relative to the probe so as to spread the engagement features of the snares away from one another in lateral directions transverse to the forward direction.

In some examples, the step of moving the snares relative to the probe includes inflating a spreader balloon disposed between the snares. The step of moving the snares and the implant toward the stop element may include operating a movement element connected between the snares and the probe to move the snares relative to the probe in a rearward direction opposite to the forward direction.

In some embodiments, a device for repositioning an implant within a lumen of a subject may include (a) a catheter having forward and rearward ends and a collapsible and expansible stop element mounted adjacent the forward end of the catheter, the stop element being adapted to engage a wall of the lumen when expanded and to provide one or more passages extending from a rear side of the stop element to a forward side of the stop element when the stop element is expanded and engaged with the wall of the lumen and (b) one or more snares, each snare having engagement features, the stop element and the snares being constructed and arranged so that the snares can be positioned extending through the one or more passages with their engagement features forward of the stop element and so that the snares can be engaged with the implant and retracted rearwardly relative to the stop element while the stop element is engaged with the wall of the lumen.

In some example, the device may further include an elongated probe having forward and rearward ends, wherein the one or more snares includes a plurality of snares connected to the probe adjacent the distal end thereof. The catheter may define a bore extending forwardly and rearwardly, the one or more passages defined by the stop element include a main passage communicating with the bore of the catheter, and the probe and snares are arranged so that the forward end of the probe can be advanced through the bore and main passage. The one or more snares may include a plurality of snares connected to an elongated probe, the plurality of snares and the elongated probe being configured such that moving the snares relative to the probe spread the engagement features of the snares away from one another in lateral directions transverse to a forward direction.

In some examples, the device may further include a spreader balloon disposed between the plurality of snares, wherein inflating the spreader balloon moves the snares relative to the probe. The device may further include a movement element connected between the snares and the probe and configured to move the snares relative to the probe in a rearward direction opposite to the forward direction. The stop element may include a stop balloon mounted to the catheter, the stop balloon having an inflated condition in which the stop balloon defines a peripheral surface extending at least partially around a forward-to-rearward axis of the catheter and having a diameter larger than the catheter, and one or more recesses in the peripheral surface, the recesses extending across the peripheral surface in the forward and rearward directions so that when the stop balloon is in the inflated condition, the peripheral surface is engaged with the wall of the lumen and the recesses and the wall of the lumen cooperatively define the one or more passages.

BRIEF DESCRIPTION OF THE DRAWINGS

Various embodiments of the present invention are described herein with reference to the drawings, wherein:

FIG. 3A is a schematic side elevational view of a repositioning device having a balloon;

FIG. 3B is a schematic perspective view of a balloon of a repositioning device;

FIG. 6A is a schematic side elevational view of a repositioning device having a spreader balloon in the collapsed position;

FIG. 6B is a schematic side elevational view of the repositioning device of FIG. 6A in the expanded position; and FIG. 7 is a schematic side elevational view of a repositioning device having a movement element.

Various embodiments of the present invention will now be described with reference to the appended drawings. It is appreciated that these drawings depict only some embodiments of the invention and are therefore not to be considered limiting of its scope.

DETAILED DESCRIPTION OF THE INVENTION

As used herein, the term "proximal," when used in connection with a prosthetic heart valve, refers to the portion or end of the heart valve closest to the heart when the heart valve is implanted in a patient, whereas the term "distal," when used in connection with a prosthetic heart valve, refers to the portion or end of the heart valve farthest from the heart when the heart valve is implanted in a patient. When used in connection with devices for delivering a prosthetic heart valve into a patient, the terms "proximal" and "distal" are to be taken as relative to the user of the delivery devices. "Proximal" is to be understood as relatively close to the user, and "distal" is to be understood as relatively farther away from the user.

Figure 1:
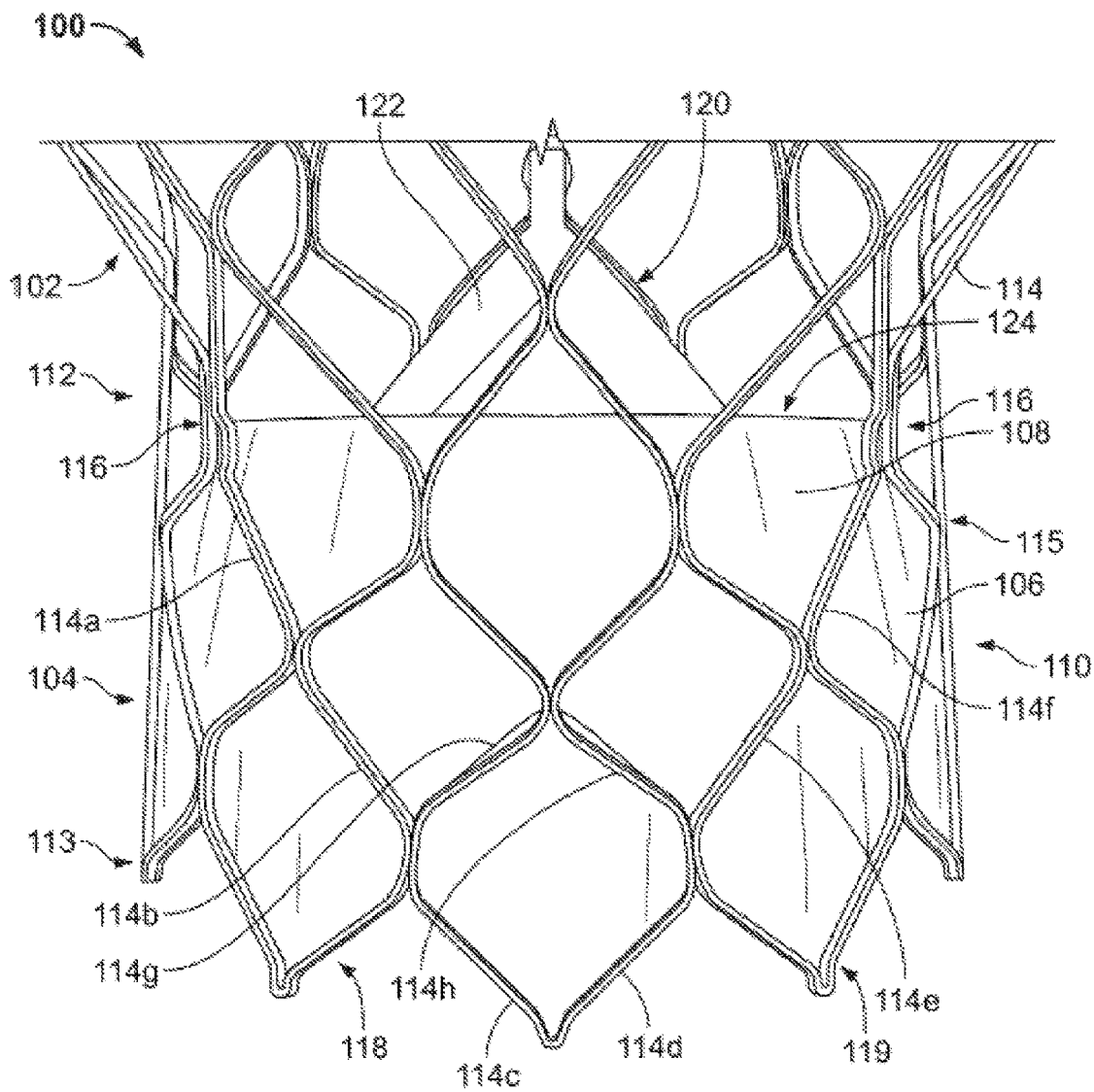
FIG. 1 is a side elevational view of a conventional prosthetic heart valve.

FIG. 1 shows a conventional collapsible prosthetic heart valve 100. The prosthetic heart valve 100 is designed to replace the function of a native aortic valve of a patient. Examples of collapsible prosthetic heart valves are described in International Patent Application Publication No. WO/2009/042196; U.S. Pat. No. 7,018,406; and U.S. Pat. No. 7,329,278, the disclosures of all of which are hereby incorporated herein by reference. As discussed in detail below, the prosthetic heart valve has an expanded condition and a collapsed condition. Although the invention is described herein as applied to a prosthetic heart valve for replacing a native aortic valve, the invention is not so limited, and may be applied to prosthetic valves for other cardiac applications.

The prosthetic heart valve 100 includes a stent or frame 102, which may be wholly or partly formed of any biocompatible material, such as metals, synthetic polymers, or biopolymers capable of functioning as a stent. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a stent include, but are not limited to, thermoplastics, such as polyolefins, polyesters, polyamides, polysulfones, acrylics, polyacrylonitriles, polyetheretherketone (PEEK), and polyaramides. The stent 102 may have an annulus section 110 and an aortic section (not shown). Each of the annulus section 110 and the aortic section of the stent 102 includes a plurality of cells 112 connected to one another around the stent. The annulus section 110 and the aortic section of the stent 102 may include one or more annular rows of cells 112 connected to one another. For instance, the annulus section 110 may have two annular rows of cells 112. When the prosthetic heart valve 100 is in the expanded condition, each cell 112 may be substantially diamond shaped. Regardless of its shape, each cell 112 is formed by a plurality of struts 114. For example, a cell 112 may be formed by four struts 114.

The stent 102 may include commissure points 116 connecting at least two cells 112 in the longitudinal direction of the stent 102. The commissure points 116 may include eyelets for facilitating the suturing of a valve assembly 104 to the sent 102.

The prosthetic heart valve 100 also includes a valve assembly 104 attached inside the annulus section 110 of the stent 102. United States Patent Application Publication No. 2008/0228264, filed Mar. 12, 2007, and United States Patent Application Publication No. 2008/0147179, filed Dec. 19, 2007, the entire disclosures of both of which are hereby incorporated herein by reference, describe suitable valve assemblies. The valve assembly 104 may be wholly or partly formed of any suitable biological material or polymer. Examples of biological materials suitable for the valve assembly 104 include, but are not limited to, porcine or bovine pericardial tissue. Examples of polymers suitable for the valve assembly 104 include, but are not limited to, polyurethane and polyester.

The valve assembly 104 may include a cuff 106 disposed on the lumenal surface of annulus section 110, on the ablumenal surface of annulus section 110, or on both surfaces, and the cuff may cover all or part of either or both of the lumenal and ablumenal surfaces of the annulus section. FIG. 1 shows cuff 106 disposed on the lumenal surface of annulus section 110 so as to cover part of the annulus section while leaving another part thereof uncovered. The valve assembly 104 may further include a plurality of leaflets 108 which collectively function as a one-way valve. A first edge 122 of each leaflet 108 may be attached to the cuff 106 or the stent 102 by any suitable attachment means, such as suturing, stapling, adhesives or the like. For example, the first edge 122 of each leaflet 108 may be attached to the cuff 106, and the cuff may in turn be attached to the stent 102. Alternatively, the first edge 122 of each leaflet 108 may be sutured to the stent 102 by passing strings or sutures through the cuff 106 of the valve assembly 104. A second or free edge 124 of each leaflet 108 may coapt with the corresponding free edges of the other leaflets, thereby enabling the leaflets to function collectively as a one-way valve.

Irrespective of the attachment means employed, the leaflets 108 may be attached to the cuff 106 or to the stent 102 along at least some struts 114 of the stent to enhance the structural integrity of the valve assembly 104. As a consequence of this attachment, the struts 114 help support the leaflets 108 of the valve assembly 104 and may therefore reduce the strain in the leaflet-cuff junction.

In operation, the embodiment of the prosthetic heart valve described above may be used to replace a native heart valve, such as the aortic valve. The prosthetic heart valve may be delivered to the desired site (e.g., near a native aortic annulus) using any suitable delivery device. Typically, during delivery, the prosthetic heart valve is disposed inside the delivery device in the collapsed condition. The delivery device may be introduced into a patient using a transfemoral, transapical, transseptal or other approach. Once the delivery device has reached the target site, the user may deploy the prosthetic heart valve. Upon deployment, the prosthetic heart valve expands, preferably into secure engagement within the native aortic annulus. When the prosthetic heart valve is properly positioned inside the heart, it works as a one-way valve, allowing blood to flow in one direction and preventing blood from flowing in the opposite direction.

Problems may be encountered when implanting the prosthetic heart valve. For example, in certain procedures, collapsible valves may be implanted in a native valve annulus but not initially placed in an ideal position. If the collapsible valve has been fully deployed (e.g., unsheathed) it may be difficult to reposition the valve in the proper location.

Improper placement of the valve may lead to a host of problem, such as: (1) perivalvular leakage (PV leak), (2) valve migration, (3) mitral valve impingement, (4) conduction system disruption, (5) coronary blockage, etc., all of which can have severely adverse clinical outcomes. To reduce these adverse events, devices may be used to reposition the heart valve after full deployment.

Figure 2B:
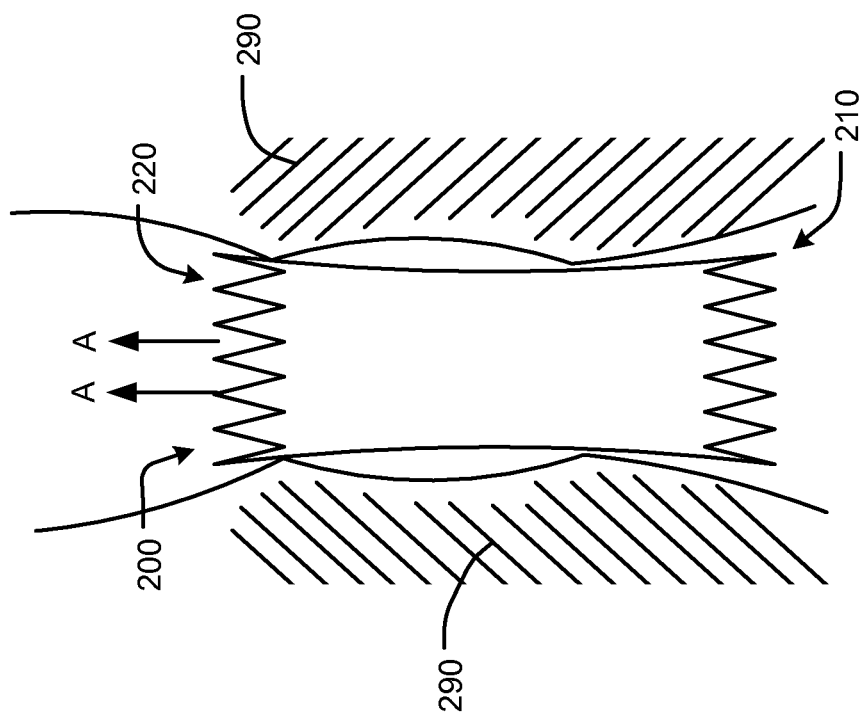
FIG. 2B is a schematic side elevational view of a prosthetic heart valve that requires repositioning in the native annulus.
Figure 2A:
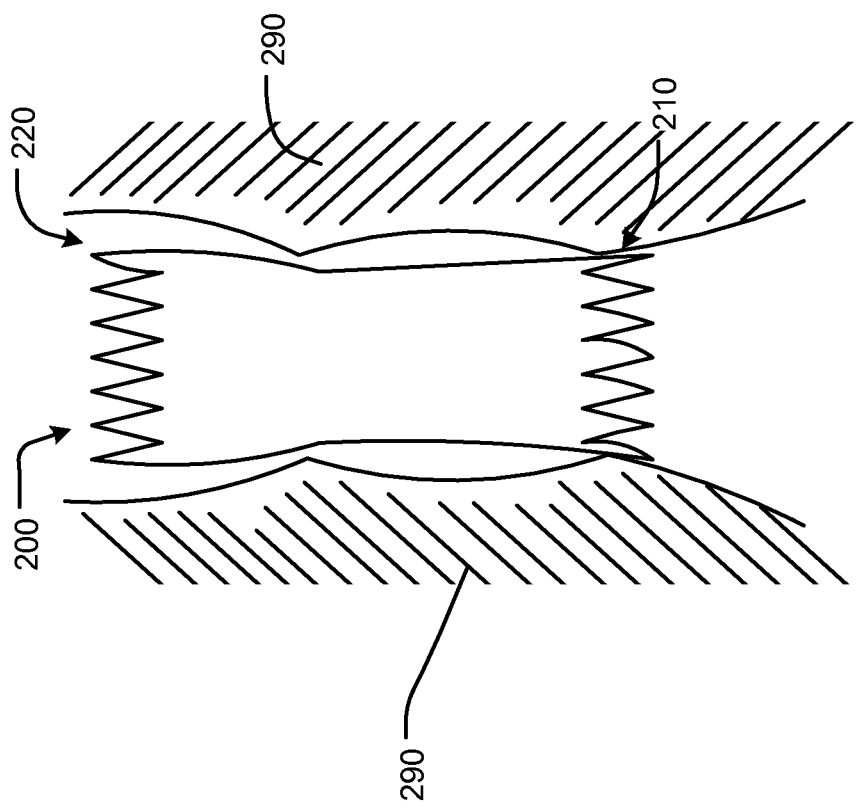
FIG. 2A is a schematic side elevational view of a prosthetic heart valve properly positioned in a native valve annulus.

FIG. 2A illustrates a prosthetic heart valve 200 positioned within a coronary artery of a patient. Specifically, as seen in FIG. 2A, heart valve 200 includes an annulus section 210 and an aortic section 220 in their fully-expanded condition. Annulus section 210 is disposed within the native valve annulus 290. It is often difficult to unsheathe heart valve 200 at the appropriate location without needing to reposition the valve slightly.

FIG. 2B illustrates a prosthetic heart valve 200 that is not properly located within native valve annulus 290, a condition that may lead to problems in operation of the valve. For example, heart valve 200 may be distorted or incapable of expanding fully resulting in a condition in which not all of the valve leaflets meet to form effective coaptation junctions. This can result in leakage or regurgitation and other inefficiencies which can reduce cardiac performance. Moreover, if the prosthetic valve 200 is not placed optimally and the valve leaflets are not coapting as intended, other long term effects, such as uneven wear of the individual leaflets, can be postulated. Thus, in such instances, heart valve 200 may require that it be shifted as indicated by arrows "A". One method of repositioning heart valve 200 requires resheathing the heart valve and redeploying it. This method may be undesirable as it increases the time of operation and the risk of additional trauma to the vasculature during deployment.

In order to avoid these problems, a valve repositioning device may be used to carefully reposition a deployed valve within the patient vasculature. The valve repositioning device may be deployed at or near the heart valve in order to reposition it. In at least some examples, the repositioning device is introduced via the aorta. Aortic techniques will be described but it should be understood that this is merely illustrative and that the valve repositioning device may be used to reposition prosthetic devices other than the prosthetic aortic valves.

FIG. 3A illustrates a valve repositioning device 300 according to a first embodiment of the present invention. The valve repositioning device 300 includes an expansible stop element 302 and a delivery catheter 350 attached to the stop element 302. In the examples shown in FIG. 3A, the stop element is a balloon made wholly or partly formed of but not limited to non-compliant materials such as polyethylene terephthalates, polyacrylenesulfide, and copolyesters or compliant materials such as polyvinyl chloride (PVC), polyurethanes, cross-linked low density polyethylenes [PETs], and highly irradiated linear low density polyethylene [LDPE] or semi-compliant materials such as nylon and polyamines.

Prior to insertion into a patient, stop element 302 may be folded into the collapsed condition, for example, using a pleat fold or a T-fold. In the collapsed condition, the diameter of stop element 302 may be about 4 mm or less. Once the repositioning device 300 has been placed in the desired position within the patient, a fluid may be injected into the stop element 302 to expand the stop element to a suitable diameter. Specifically, catheter 350 may define a bore 360 extending forwardly and rearwardly through the catheter and a conduit 355 disposed within the bore and in fluid communication with the interior of the stop element 302 for carrying a fluid from a fluid source (not shown) to the interior of the stop element via port 308. Inflation fluids may be a gas, such as helium or carbon dioxide, or a liquid, such as saline.

FIG. 3B illustrates one example of stop element 302 in its fully expanded condition. For the sake of clarity, catheter 350 and conduit 355 are not shown. As illustrated in FIG. 3B stop element 302 be a toroid or doughnut-shaped. It will be understood that stop element 302 may be formed in other shapes and other cross-sectional shapes are contemplated, including, for example, triangular, rectangular, trapezoidal, elliptical, curved, and other polygonal and non-polygonal shapes. When fully expanded, stop element 302 has a cross-sectional size that is at least equal to the cross-sectional size of the aortic sinus. This will ensure that stop element 302 fully contacts the native tissue around substantially the entirety of the sinus. Optionally, the toroid-shaped stop element 302 includes one or more passages through which a snare may be passed to maneuver an implant. FIG. 3B illustrates a stop element having a passage in the form of a central aperture 310. Central aperture 310 of stop element 302 may allow additional devices, such as snares described with reference to FIGS. 4-5, to be deployed to reposition heart valve 200.

Stop element 302 may serve as a backstop or anchor when repositioning prosthetic heart valve 200. Specifically, as seen in FIG. 3A, stop element 302 may be positioned in the aorta to prevent heart valve 200 from migrating into the aorta during repositioning.

Figure 4C:
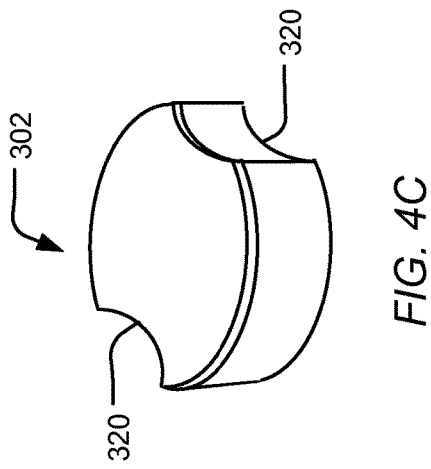
FIG. 4C is a schematic perspective view of the balloon illustrated in FIG. 4B.
Figure 4B:
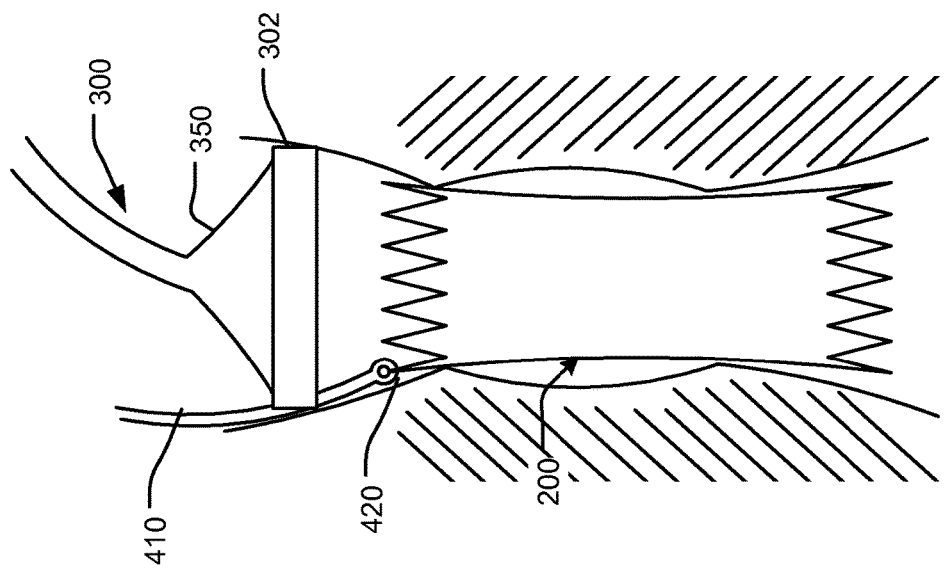
FIG. 4B is a schematic side elevational view of a second example of a repositioning device having a balloon and a snare.
Figure 4A:
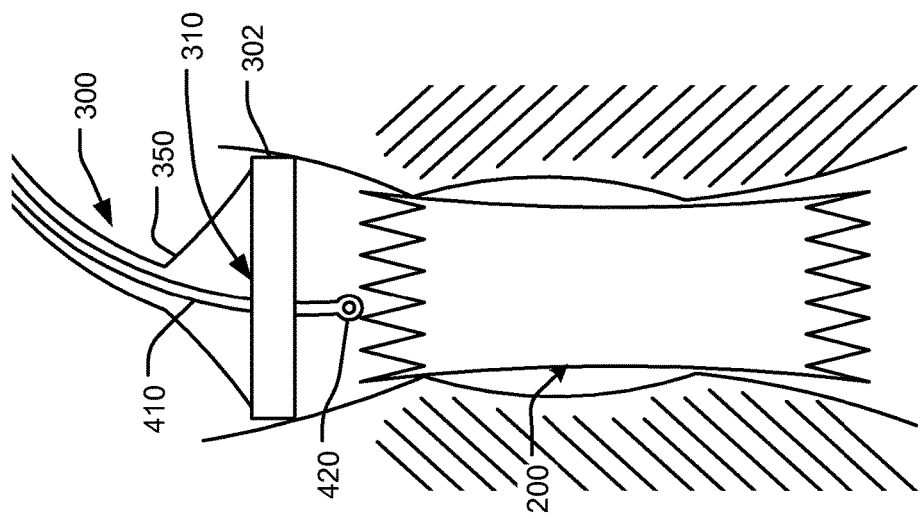
FIG. 4A is a schematic side elevational view of a repositioning device having a balloon and a snare.

FIGS. 4A and 4B illustrate a valve repositioning device including a catheter coupled to a stop element and a snare. The devices are used to reposition heart valves within the aortic sinus.

As seen in FIG. 4A, snare 410 may be introduced through central aperture 310 of stop element 302. With this configuration, stop element 302 may be securely anchored against the walls of the native valve annulus to prevent heart valve 200 from traveling into the aorta should the snare 410 pull the heart valve too far upward. Snare 410 may be formed as a wire (e.g., a guidewire) having an engagement feature 420 for coupling to a portion of the prosthetic heart valve 200. Engagement feature 420 may include any type of coupling mechanism such as a hook, clip or tab for coupling to a portion of the stent or prosthetic heart valve to reposition it. In at least some examples, snare 410 includes an engagement feature 420 in the shape of a circle to couple to a tab on the stent. Snare 410 may be used to reposition heart valve 200 by pulling the heart valve while stop element 302 prevents the heart valve 200 from going too far into the aorta.

Snare 410 may be wholly or partly formed of any biocompatible material, such as metals, synthetic polymers, or biopolymers. Suitable biopolymers include, but are not limited to, elastin, and mixtures or composites thereof. Suitable metals include, but are not limited to, cobalt, titanium, nickel, chromium, stainless steel, and alloys thereof, including nitinol. Suitable synthetic polymers for use as a snare include, but are not limited to, thermoplastics, such as polyolefins, polyesters, polyamides, polysulfones, acrylics, polyacrylonitriles, polyetheretherketone (PEEK), and polyaramides.

The following will describe the use of a repositioning device for properly positioning an implant, in this case a prosthetic heart valve. As an initial step, stop element 302 of repositioning device 300 may first be inserted into the patient in the collapsed condition and advanced to the desired site for valve repositioning at location offset from the implant. For example, repositioning device 300 may be inserted into the patient's vasculature and advanced near the aorta and the site of the native aortic valve. If the repositioning device 300 includes echogenic materials, it may be guided to the appropriate position using the assistance of three-dimensional echocaradiography to visualize the repositioning device 300 within the patient.

Once repositioning device 300 has reached the desired site, stop element 302 may be inflated to assume an expanded shape by introducing a fluid through fluid conduit 355. With stop element 302 in its expanded condition, central aperture 310 is formed through which snares 410 may be introduced. Snares 410 may be passed from the catheter 350 through a passage such as a central aperture and engagement features 420 may mate with a portion of the implant. Snares 410 may then be actuated as desired to reposition heart valve 200 into its optimum or desired position. Upon repositioning of heart valve 200, snares 410 may be detached from the heart valve and pulled back through central aperture 310 and into catheter 350. Stop element 302 may be collapsed by removing the fluid therefrom and the repositioning device 300 may be removed from the patient's body. While the operation of the repositioning device 300 of FIG. 4A has been described, it will be understood that other examples described may be implemented in a similar manner.

FIGS. 4B and 4C illustrate a second example of a stop element and snare assembly. As seen in FIG. 4B, with stop element 302 in position at the aorta, a snare 410 may be passed alongside stop element 302 to reposition heart valve 200. Instead of a passage in the form of a central aperture, stop element 302 may include one or more concave portions 320 on the periphery. One exemplary stop element 302 having two concave portions 320 is shown in FIG. 4C. Concave portions 320 form passages between the stop element and the wall of the lumen through which snares may be advanced. It will be understood that stop element 302 and snare 410 may be combined into a single repositioning device or may be formed, introduced and/or actuated separately.

Figure 5:
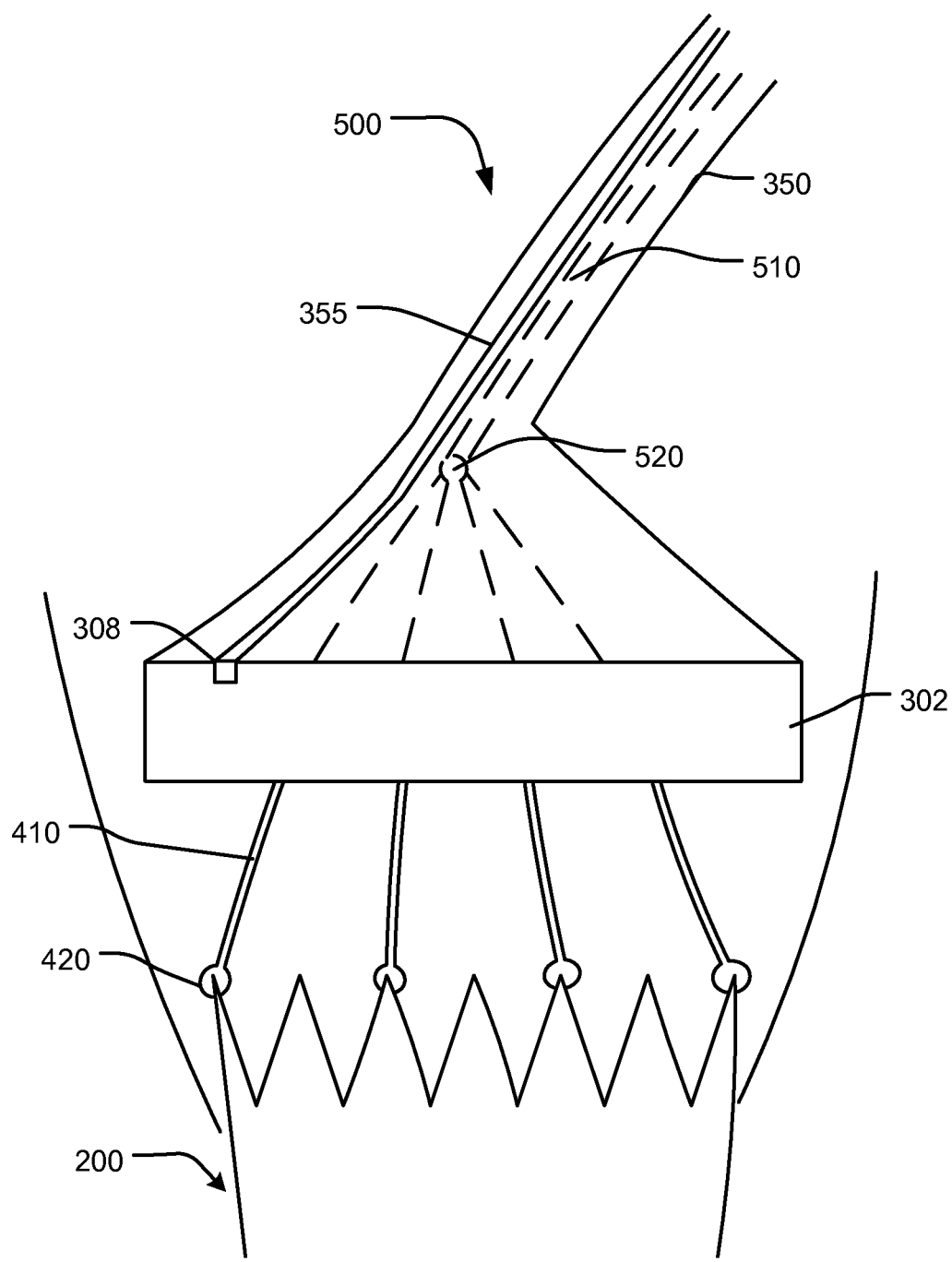
FIG. 5 is a schematic side elevational view of a repositioning device having a balloon and multiple snares.

FIG. 5 illustrates a valve repositioning device 500 having an expandable stop element 302 attached to a delivery catheter 350 and multiple snares 410 passing through the central aperture 310 of stop element 302. By employing multiple snares 410, the position of valve 200 may be uniformly adjusted and uneven repositioning may be avoided. Any number of snares 410 may be used at necessary. In at least some examples, one, two, three, four, five, six, seven or eight snares 410 may be used to reposition heart valve 200.

As seen in FIG. 5, snares 410 may be evenly distributed to attach to portions of stent 220. In at least some examples, even distribution of snares 410 may be accomplished by evenly distributing snares 410 about the circumference of stent 220. For example, two snares 410 may be diametrically opposed on stent 220. Three snares 410 may likewise be attached 120 degrees apart from each other about stent 220 to accomplish even repositioning of heart valve 200. Snares 410 may be actuated independently such that the user may pull a single snare 410 to reposition an end of heart valve 200. In at least some other examples, snares 410 may be actuated together. Snares 410 may be connected to an elongated probe 510 and joined to a single node 520. Pulling or actuating elongated probe 510 may serve to actuate all snares 410 at the same time. Snares 410 may be resilient and outwardly biased so that when deployed through stop element 302, snares spread outwardly, away from one another in lateral directions transverse to a forward direction.

All or part of the repositioning device, such as the stop element, delivery catheter and/or snares, may be made of one or more echogenic materials to enable these structures to be more easily visualized using three-dimensional echocardiography while the device is in use in a patient. This allows the physician or surgeon to more easily maneuver, monitor and retract the device without any injury to the patient.

FIG. 6A illustrates another embodiment of a repositioning device 300 in a collapsed condition. Instead of biasing the snares, a spreader balloon may be used to manipulate the snares. As shown in this figure, repositioning device 300 is similar to that describe above, but includes a spreader balloon 610 disposed between the snares 410. Elongated probe 510 may further define a channel 620 in fluid communication with spreader balloon 610 and configured to inflate it. Channel 610 may run along the length of bore 360 of catheter 350.

FIG. 6B illustrates the repositioning device 300 of FIG. 6A in its expanded condition. As seen in FIG. 6B, as spreader balloon 610 begins to inflate, it begins to take on a less-elongate expanded configuration. Specifically, spreader balloon 610 widens and shortens to assume its expanded configuration and snares 410 begin to spread outwardly, away from one another in lateral directions transverse to a forward direction. Thus, instead of having biased snares, snares 410 may be manipulated using a spreader balloon 610.

In operation, stop element 302 may be introduced into a vessel, such as the aorta, in the deflated configuration. Stop element 302 may be inflated using a gas or fluid through conduit 360 and snares 410 may be advanced through central aperture 310 of the stop element. Spreader balloon 610 may then be inflated to outwardly push snares 410 until engagement feature 420 of snare 410 couple to a portion of an implant, such as a heart valve. The implant may be repositioned as needed by pulling on the elongated probe. Once the implant has been properly positioned, spreader balloon 610 may be deflated to decouple the engagement features of the snares from the implant. Stop element 302 may then be deflated and the catheter, stop element and snares retrieved and removed from the patient's body.

FIG. 7 illustrates another embodiment of a repositioning device 300 in a deployed condition. In this embodiment, a movement element 650 is connected between snares 410 and elongated probe 510 and configured to move the snares relative to the probe in a forward direction toward the implant and a rearward direction opposite the forward direction. Movement element 650 may be actuated by a button on handle at the proximal end of the catheter (not shown). The movement element may include an inflatable element or any other movement mechanism. Operation of this variation is similar to that described with reference to FIGS. 6A and 6B. However, instead of retracting the elongated probe, the user may actuate the movement element 640 causing the snares to move in the rearward direction toward the stop element to reposition the implant. It will be understood that this configuration may be modified in any of the methods describe above. For example, a configuration may be made that utilizes both a movement element and a spreader balloon. Additionally, the shape and size of stop element may be modified as necessary.

It will also be noted that while the inventions herein are predominately described in connection with the replacement of a tricuspid valve, the inventions are equally applicable to the replacement of other valves, including a bicuspid valve, such as the mitral valve. Moreover, the snares could have different shapes, or engagement features depending on the devices being repositioned.

Moreover, although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A device for repositioning an implant within a lumen of a subject comprising:
   (a) a catheter having forward and rearward ends and a collapsible and expansible stop element mounted adjacent the forward end of the catheter, the stop element being adapted to engage a wall of the lumen when expanded and having a central passage defined by an inner wall of the stop element that extends from a rear side of the stop element to a forward side of the stop element when the stop element is expanded and engaged with the wall of the lumen, the central passage having a circular cross-section and a constant diameter from the forward side to the rear side of the stop element; and
   (b) one or more snares, each snare terminating in engagement features at distal ends thereof for mating with the implant, the stop element and the snares being constructed and arranged so that the snares are freely movable within the circular cross-section of the central passage and able to contact the inner wall of the stop element with their engagement features forward of the stop element and so that the snares can be engaged with the implant and retracted rearwardly relative to the stop element while the stop element is engaged with the wall of the lumen;
   wherein the one or more snares includes multiple snares, and wherein each of the engagement features is a hook having a free end, the free ends of the hooks being unconnected to one another.

2. A device as claimed in claim 1, wherein the stop element includes an inflatable stop balloon.

3. A device as claimed in claim 2, wherein the inflatable stop balloon further comprises a port in fluid communication with an interior of the stop balloon for receiving a fluid to inflate the stop balloon.

4. A device for repositioning an implant within a lumen of a subject comprising:
   (a) a catheter having forward and rearward ends and a collapsible and expansible stop element mounted adjacent the forward end of the catheter, the stop element being adapted to engage a wall of the lumen when expanded and having a central passage defined by an inner wall of the stop element that extends from a rear side of the stop element to a forward side of the stop element when the stop element is expanded and engaged with the wall of the lumen, the central passage having a circular cross-section and a constant diameter from the forward side to the rear side of the stop element; and (b) one or more snares, each snare terminating in engagement features at distal ends thereof for mating with the implant, the stop element and the snares being constructed and arranged so that the snares are freely movable within the circular cross-section of the central passage and able to contact the inner wall of the stop element with their engagement features forward of the stop element and so that the snares can be engaged with the implant and retracted rearwardly relative to the stop element while the stop element is engaged with the wall of the lumen, wherein the one or more snares includes multiple snares, and wherein the implant is a prosthetic heart valve having a metallic stent, and each of the engagement features is independently moveable and configured to couple to a portion of the stent.

\* \* \* \* \*